United States Patent [19]

Ludwa et al.

[11] 4,276,338
[45] Jun. 30, 1981

[54] ABSORBENT ARTICLE

[75] Inventors: Raymond J. Ludwa, Fairfield; Mark E. Forry, Mason; Marilyn M. Haugen, Fairfield, all of Ohio

[73] Assignee: The Procter & Gamble Company, Cincinnati, Ohio

[21] Appl. No.: 35,141

[22] Filed: May 1, 1979

[51] Int. Cl.³ .......................... B32B 5/12; B32B 5/14
[52] U.S. Cl. ................................ 428/137; 15/209 R; 428/138; 428/198; 428/218; 428/332
[58] Field of Search ............... 428/218, 154, 198, 284, 428/207, 332, 137, 171, 138; 162/111, 132; 15/209 R; 128/284, 290 R, 290 P

[56] References Cited

U.S. PATENT DOCUMENTS

| | | | |
|---|---|---|---|
| 3,017,304 | 1/1962 | Burgeni | 162/132 |
| 3,708,366 | 1/1973 | Donnelly | 428/198 |
| 4,027,672 | 6/1977 | Karami | 128/284 |
| 4,135,024 | 1/1979 | Callahan et al. | 428/171 |
| 4,144,370 | 3/1979 | Boulton | 428/233 |
| 4,154,883 | 5/1979 | Elias | 428/218 |
| 4,186,463 | 2/1980 | Marshall | 19/304 |

Primary Examiner—Paul J. Thibodeau
Attorney, Agent, or Firm—L. Williamson; R. L. Hemingway; R. C. Witte

[57] ABSTRACT

An absorbent article or portion thereof comprises first and second layers joined together intimately in a generally parallel and coextensive manner. Each layer has a pattern of multiple discrete holes or regions of low density which are separated by regions of high density. The layers are aligned to minimize the number of holes or regions of low density of one layer which substantially overlap one or more holes or regions of low density of the other layer. The articles are characterized by better wicking, lower thermal conductivity and improved appearance compared to articles in which a higher degree of overlap of low density areas is noted.

A process for making absorbent articles having improved wicking is also disclosed. This process is carried out by aligning the adjacent layers of the absorbent body as described above.

20 Claims, 3 Drawing Figures

ABSORBENT ARTICLE

TECHNICAL FIELD

Most broadly, the present invention relates to absorbent articles and elements having improved wicking rates, and to a method for making such articles. The invention specifically relates to absorbent sheets and sheet-like materials.

BACKGROUND OF THE INVENTION

Various absorbent materials have been used and manufactured in the past for the purpose of absorbing fluids in order that the fluids may be used, stored, transported, or discarded conveniently. Such articles exist in myriad forms; a short list would include wiping cloths, diapers, tampons, towels, surgical drapes, articles of clothing, cleaning implements, bandages and dressings, and so forth.

A frequent shortcoming of many such articles is the rate at which they are able to wick the fluid being absorbed away from the point at which such fluid initially contacts the article. This property is crucial to effective absorbency because wicking determines how rapidly and well the article can distribute a liquid among its absorbent elements. Even a material with adequate absorbent capacity cannot retain the maximum amount of fluid unless the fluid is distributed throughout the absorbent portions of the article before it can escape from the article.

Workers in the art have consistently attempted to reduce the amount of absorbent material in absorbent articles to a minimum effective level, in order to make absorbent articles having minimal bulk, weight, and raw material cost. This trend is especially evident in the case of disposable absorbent materials. Accordingly, those skilled in the art have needed to produce absorbent articles and structures which efficiently wick liquid to distribute it throughout the article and thus to optimize the use of absorbent material in the article.

Various types of layered structures have been devised in the quest to produce better absorbent materials, particularly disposable towels or wipes. A common example of such a structure is the ordinary two-layer paper towel. Perforated nonwoven materials have also been made for a considerable time and sold for use as disposable dishrags, towels, and so forth. An example of such a product is HANDI-WIPES, a product sold commercially by The Colgate-Palmolive Company, New York, N.Y.. However, it is desirable to improve such products as absorbent materials, for none of them are ideal.

Another property of a towel or wipe which has been found to be useful is that of limited conductivity of heat. Durable wipes, such as conventional bar swipes, are frequently used in the restaurant trade as makeshift potholders to handle hot pans and utensils safely. While prior art disposable wipes have been marketed for some time, and have been recognized to have the advantages of convenience and low capital cost, one factor which prevents them from capturing the durable wipes market is their unsuitability as potholders. Accordingly, it has been found that a nonwoven material which has low thermal conductivity will be more suitable as a wipe, particularly if it does not require more raw material and bulk in order to serve as an efficient insulator.

Finally, a third property which is desirable in a wipe, and which has been absent in prior art disposable wipes, is an opaque appearance. Durable wipes typically are opaque, (or at least more so than existing disposable wipes) so opacity is associated with quality, appropriate bulk, strength, and other desirable characteristics of a wipe.

DISCLOSURE OF THE INVENTION

The first aspect of the present invention is an absorbent article or surface comprising two adjacent layers of absorbent material joined together in a generally parallel and coextensive alignment, so that a major face of one layer is brought into intimate contact with a major face of the other layer. The first layer of material comprises an absorbent sheet of fibrous material which has a multiplicity of discrete regions of low density penetrating through its thickness; these regions of low density are separated by regions of high density. The second layer of material comprises an absorbent sheet or surface of fibrous material which has a multiplicity of discrete regions of low density, separated by regions of high density. The low density regions, preferably (but do not necessarily) extend through the thickness of the second layer. The first and second layers are aligned to minimize the percentage of low density regions of the first layer which substantially overlap low density regions of the second layer; this orientation is maintained by extensively bonding the two layers together using discontinuous bonds. The absorbent structure of the present invention is characterized by a percentage of overlap of low density regions of the respective layers which is lower than the percentage of overlap which would be observed if the absorbent layers were bonded without aligning them as taught herein. The wipes which have a low degree of overlap have been found to demonstrate superior wicking performance.

A second aspect of the present invention is a method to produce wipes which consistently deliver improved wicking performance. To practice this method, first and second layers of absorbent material are provided which have the high and low density regions indicated previously. These materials are aligned so that a major proportion of the low density areas of said first layer do not substantially overlap one or more low density areas of said second layer. (In an optimized, and thus highly preferred, embodiment of the present method the layers of absorbent material are aligned so that substantially none of the low density areas of the first layer overlap a low density area of the second layer, since it has been found that the less overlap present, the better the wicking properties of the finished sheet.)

When the first and second layers of absorbent material are aligned as described, the alignment is maintained while the first and second layers are bonded together to form a structure in which the joined major faces of the respective layers are maintained in intimate contact. Areas of bonding must be close enough together to maintain the orientation of the low density areas of the sheets, while being sufficiently unobstrusive to avoid interference with the absorbent qualities of said first and second layers of absorbent material.

In a variation of the method described above the alignment step is performed, after the other steps are completed, by selecting from a group of randomly aligned two-layer structures those structures which exhibit a low degree of overlapping.

DESCRIPTION OF PREFERRED EMBODIMENTS

Figure 1:
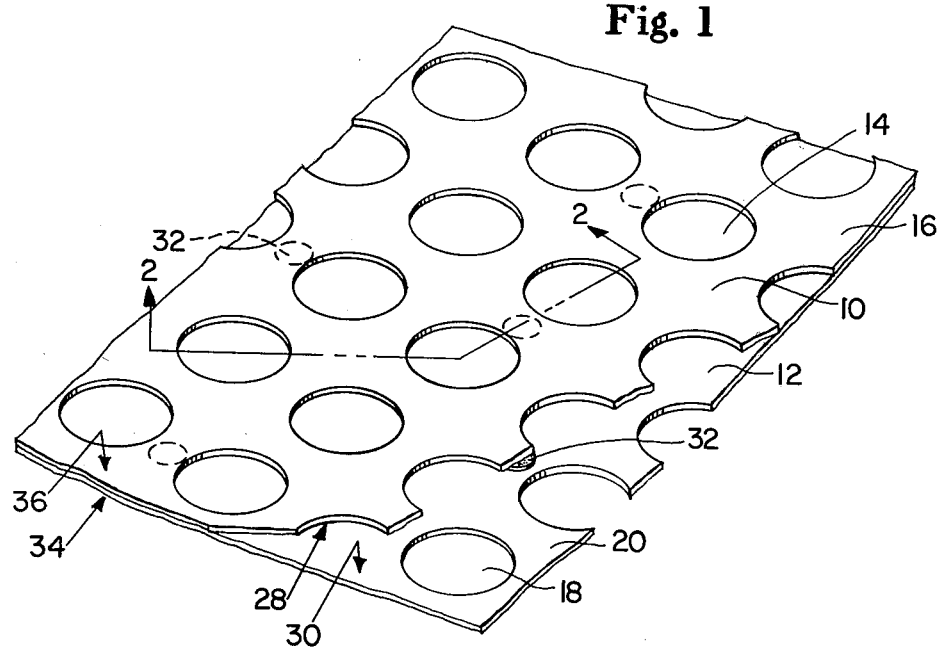
FIG. 1 is a greatly enlarged fragmentary perspective view of a two-layer sheet which embodies the present invention, showing the arrangement of low density regions of one of the layers.

The following description of the preferred embodiments of the present invention is presented in order to explain to those skilled in the art how to make and use the present invention, and to identify preferred embodiments of the invention. Descriptions of certain embodiments or the identification of preferred embodiments of the invention are not intended to limit the scope of the invention, which is identified in the claims which conclude this specification.

In order to make the description of the invention more clear, the following definitions are provided:

Low density means a density of 0 to 0.45 grams per cubic centimeter (g/cc), preferably 0 to 0.2 g/cc. A low density area or region is a discrete portion of material with an average density within the defined range. A low density area may be an aperture or cavity without departing from this definition.

High density means a density of 0.05 to 1.52 g/cc; a high density area or region is a portion of material with an average density within the defined range, which is additionally characterized by a density which is at least 10% greater than the density of an associated low density area or region of the same material.

A region of a first layer is said to substantially overlap a region of a second layer if, when viewed from a direction perpendicular to the major faces of the layers, the area of apparent intersection of the regions is at least as great as about 25% of the area of the region of the first layer. For example, in FIG. 3 a first layer 10 of sheet material is shown to overlie a second layer 12 of sheet material. First layer 10 has a low density region 14 and a high density region 16. Second layer 12 of sheet material has a low density region 18 and a high density region 20. First layer 10 and second layer 12 are parallel to the page. When viewed from a direction perpendicular to the page, low density region 14 of sheet 10 is apparently divided into region 22, which does not overlap low density region 18 of second layer 12, and region 24 which overlaps (and in this view appears to define a region of intersection with respect to) low density area 18 of second layer 12. Region 26 defines the portion of low density region 18 of second layer 12 which does not underlie or appear to intersect with low density region 14 of first layer 10.

Figure 3:
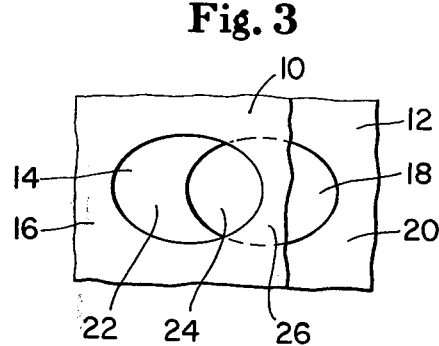
FIG. 3 is a highly schematic view of a low density area of a first layer which overlaps a low density area of an underlying second layer.

It will be apparent from an inspection of FIG. 3 that low density region 14 of first layer 10 substantially overlaps low density region 18 of second layer 12 because the area of region 24 defining the overlap of low density regions 14 and 18 is more than 25% of the area of low density region 14 of first layer 10.

A percentage of overlap in a layered material is defined as 100 times the ratio of the number of low density regions of the top layer which substantially overlap underlying low density regions to the total number of low density regions in the top layer of the material in question. For example, if the first layer of a sample of material has 25,000 low density regions, and 10,000 of those regions substantially overlap low density regions of an underlying adjacent layer, the percentage of overlap is given by the following calculation:

$$\text{percentage of overlap} = 100\% \times \frac{(10{,}000 \text{ overlapping regions})}{(25{,}000 \text{ total regions})}$$

$$\text{percentage of overlap} = 40\%$$

Procedures by which to determine percentage of overlap are provided in the examples, although it shall be understood that the present definition defines percentage of overlap for purposes of delineating the scope of the present invention.

Generally parallel as used herein is defined as a relation between the major faces of two layers of material in which the respective major faces have substantially identical contours in adjacent regions and are separated one from the other by substantially the same distance over the entire extent of their overlap.

The span of a region is defined herein as the length of a line segment passing through the region and having endpoints at the two points of the perimeter of the region which the line segment intersects. The span of a low-density region shall be defined herein as the length of the line segment noted above; the line further defining said line segment shall be a line joining the center of the low density region to the center of the nearest adjacent low density region. The span of a portion of the high density region shall be defined as the length of the line segment which has as its endpoints the boundaries of the selected high density region. The line further defining this line segment shall pass through the centers of the low density regions which define the edges of the high density area.

The working face of a cleaning implement shall be defined as any major face of an implement which is designed to be a site of absorption. For example, each major face of an ordinary paper towel can be a working face, while in a conventional sponge mop having a sponge element attached at a major face to a backing plate, the major face attached to the backing plate is not a working face.

THE INDEPENDENT LAYERS

As the "Disclosure of the Invention" section indicates, the present invention is a two-layer structure wherein the layers are aligned in a certain way. What immediately follows is a description of the necessary and preferred characteristics of the individual layers which may be incorporated into structures made in accordance with the present invention.

The individual layers which are useful to practice the present invention may most broadly be defined as first and second sheets or surfaces of fibrous material which each have at least one major face capable of being intimately bonded to a major face of the other layer.

The material of each layer may be woven, knitted, or nonwoven, although nonwoven materials are preferred for use herein. The materials may be made by any of the processes which are known or may become known in the art for producing absorbent fibrous materials. The fibers which comprise the material of each layer may be made of rayon, polyester (primarily in blends), wood pulp, cotton, other natural or synthetic fibers which have utility in absorbent structures, blends of different types of the above fibers, or fibers made from materials which are mixtures of the materials of the above fibers. The fibers may have any dimensions which are useful to provide absorbent qualities to the layers.

While preferred materials for use as layers herein are made in the form of thin sheets with opposed, generally parallel major faces, one of the layers may be the exterior major face of a three-dimensional surface or bulk object. For example, the curved exterior face of a cylinder or an exterior face of a felted batt of fibers can be layers within the scope of the present invention.

Each of the layers intended for use herein must have multiple discrete regions of low density distributed on the major face which is to be laminated to the second layer. These regions must be separated by regions of high density.

The regions of low density have a density as defined above. A preferred low density region is an aperture or cavity, and a most preferred low density region is an aperture. The proportion of the layer's area which comprises low density regions is about 10% to about 60% of the surface area of the layer, preferably 15% to 30% of the surface area of the layer. The shortest span which can be defined for a low density region must be at least about 1/64 inch (0.40 mm), while the longest span which can be defined for a low density region must be at most about ½ inch (13 mm). Within the scope of the present invention, the low density area can be a pocket or cavity in the surface of a high density structure, an aperture or slit in a high density sheet, an area of few or widely spaced fibers, and so forth. The discrete regions of low density in the layers may be arranged in any pattern or randomly, so long as a large number of such regions are dispersed widely on the layer. In a preferred mode of practicing the present invention the low density areas are arranged in a regular pattern to simplify the alignment and laminating steps described hereinafter. In the event that the low density areas are arranged in a pattern, any convenient pattern may be chosen within the scope of the present invention. For example, the pattern may be a rectilinear array, a hexagonal array, a diagonal array, an array of small circles, and so forth.

The regions of high density have the density defined above, and are at least 10% more dense than the adjacent regions of low density. While the high density regions may be discontinuous, for example in a "checkerboard" pattern of high and low density regions, the preferred layers have a continuous high density region which surrounds discontinuous low density regions. Another pattern limitation relating both to high and low density regions is that the span of the portion of the high density region embraced by adjacent low density regions must be at least one half as long as the span of each embracing low density region which is defined by the same line which defines the span of the portion of the high density region described immediately above.

Those skilled in the art are able to make layers having the interspersed high and low density regions described above in a variety of ways. For example, a web of material with relatively mobile fibers may be formed and then rearranged by needles, jets of air or water or the like to form a low-density region, followed by a binding step in which the mobility of fibers in the web is reduced in order to preserve the pattern. Other ways to manufacture layers suitable for use herein will be readily found using existing technical knowledge.

Specific preferred materials which may be used as layers within the scope of the present invention are certain of the SONTARA nonwoven materials marketed by The E. I. DuPont De Nemours Company, and CHIX wipes, which are non-woven one-layer disposable wipes sold by Chicopee Mills, Inc.

THE TWO-LAYER STRUCTURE

The essence of the structure of the present invention is an absorbent body comprising two adjacent layers (as described above) intimately joined together in a generally parallel and coextensive alignment, so that a major face of a first layer is intimately laminated to a major face of a second layer. The low density regions of the first layer are arranged, with respect to the low density regions of the second layer, so that the percentage of overlap of low density regions of the respective layers is minimized.

Figure 2:
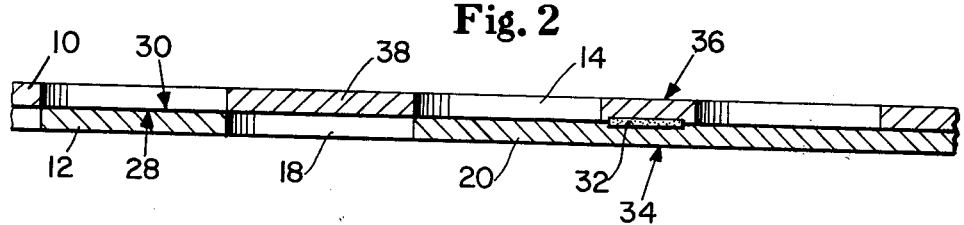
FIG. 2 is a cross-sectional view, taken along line 2—2 of FIG. 1, of a two-layer sheet which embodies the present invention.

An especially preferred embodiment of the present invention is shown in some detail in FIGS. 1 and 2. As has already been described in connection with FIG. 3, a first layer 10 of sheet material overlies a second layer 12 of sheet material. First layer 10 has low density regions such as 14 and a high density region 16. Second layer 12 of sheet material has low density regions such as 18 and a high density region 20.

Adjacent major faces 28 and 30, respectively defining surfaces of layers 10 and 12, are intimately bonded together by point bonds such as 32 to form a unitary structure. The unitary structure has opposed major faces 34 and 36, either or both of which can be working faces in this embodiment of the invention.

The structure shown in FIG. 2 is an idealized illustration of low density regions, such as 14 and 18 (in this case, apertures) of one layer which are so aligned that they are adjacent high density regions such as 20 and 38 of the adjacent layer. There is substantially no overlap between the low density regions such as region 14 of layer 10 and the low density regions such as region 18 of layer 12.

In a most preferred embodiment of the invention the percentage of overlap of the low density regions of the respective layers is zero. It is difficult, however, to effect a complete lack of overlap of the first and second layers of the absorbent material (although it is possible to do so by hand, or if extreme care is taken.) Accordingly, a percentage of overlap of greater than zero may be tolerated, although at the expense of some loss of performance. The maximum level of overlap within the scope of the present invention is defined by a random orientation of the layers, in which the first and second layers are joined without regard to the alignment of the holes and analyzed for percentage of overlap. A preferred maximum level of overlap is a percentage of overlap which is slightly less than the percentage of overlap observed in a randomly aligned structure. Clearly outside of the scope of the present invention are two-layer structures in which all of the low density regions substantially overlap.

Certain properties must be present in order for an absorbent body to be within the scope of the present invention. First, the major faces of the respective layers which are joined together must be immediately adjacent each other, so that the amount of intermediate material must be minimal if the invention is to function properly. This is not to exclude the possibility that a minor amount of such things as powdered "super-sorbers" (e.g.—starch—acrylonitrile copolymers and the like) may be disposed between the layers. It will be understood, however, that to the extent that intermediate materials prevent a major portion of the respective major faces from intimately contacting each other, such structures will be outside of the scope of the present invention.

Second, the joined major faces of the respective layers must be placed and maintained in intimate (i.e.— touching) contact over a major portion of their coextensive surfaces. Any substantial, extensive gap between the layers will prevent transfer of absorbed fluids from one layer to the other, and will thus minimize the cooperation between the first and second layers which is essential to the present invention.

Third, at least one face of one of the layers, defined herein as a working face, must be accessible to the fluid to be absorbed, for otherwise the structure would have no utility as an absorbent material. The layer defining the working face must also have low density areas which connect or communicate between the working face and the adjacent layer of material.

Fourth, the structure must be capable of substantially retaining its novel alignment while in use, in order that the laboratory measured benefits of improved absorbent performance will be retained in real-world structures which embody the present invention.

Finally, as is evident from the preceding description, the layered structure, although bound into a fairly rigorous alignment of layers, must retain its absorbent properties as a finished structure.

Given these requirements, many variations in the layered structure may be produced within the scope of the present invention.

In one (highly preferred) mode of the present invention, two identical layers of sheet material are laminated to form a "two-sided" sheet of which each (exterior) opposed major face is a working face.

In another mode of practicing the present invention, two nonidentical layers of materials are joined together to form a laminar structure which may have one or more working faces, depending on whether one or more exterior major faces have all of the necessary attributes of a working face.

Without departing from the present invention, the two-layer structure described herein may have additional layers juxtaposed to its exterior portions. A first example of such a layer is a further absorbent layer on the side of the novel structure of the present invention away from the working face thereof, to increase the absorbent capacity of the structure. A second example of additional layers is a structure in which the two layers of the present invention occupy an interior region of an absorbent body, so that absorbent layers are found exterior to each working layer of the absorbent structure of the present invention. The utility of such a disposition of the structure of the present invention would be to distribute a fluid which has already been captured by the absorbent body. (It will be realized in connection with the immediately preceding embodiment that a "working face" as defined herein need not be an exterior face of the ultimate absorbent article.)

In another embodiment of the invention a layer may be interposed between a working face of the structure of the present invention and the fluid which is to be treated with the absorbent body. For example, an open scrim of abrading material may be juxtaposed to a working face of the present structure to increase the longevity and utility of the completed article to scrub surfaces.

Dissimilar materials may be joined as taught herein in order to provide an absorbent structure with special properties. For example, materials with differing hydrophilicity or pore size may be joined as taught herein to produce a composite material with a desirable hydrophilicity or pore size gradient.

Articles having many shapes and configurations may be made which incorporate the features of the present invention. As described above, the preferred embodiment of the invention comprises two flat, generally parallel coextensive layers joined together to form a two-sided structure. But this does not limit the spectrum of possible structures.

For one example, a structure of the present invention may comprise a thin sheet of material having a working face and an opposed major face, the latter of which is attached to a major face of a three dimensional shape which defines a surface meeting the requirements of a layer as defined herein. In this case the three-dimensional shape could be a single layer, only part of which (an exterior surface) had the attributes of a layer required herein, without departing from the scope of the present invention.

The inventive structure may be attached to a handle or other implement to perform a cleaning or wiping function without departing from the structural requirements of the invention. Similarly, the structures of the present invention may be incorporated as one or more portions of a complete absorbent article, for example, as a series of discrete regions of a wipe.

The requirement of bonding of the respective layers was noted above; the two layers central to the present invention must be extensively bound together to maintain most or all of the low density regions of the structure in the indicated alignment. Numerous bonding schemes may be devised to meet this alignment need without substantially diminishing the absorbent capacity and efficiency of the layers. In a preferred mode of practicing the invention discontinuous bonding is employed, which means that a multiplicity of discrete bonds are distributed over the inner surfaces of the layers, separated by regions (preferably a continuous region) of unbonded material.

Many techniques of bonding webs together to form absorbent structures are known, so no attempt will be made to catalogue every such technique. Suffice it to say that among the bonding techniques which are useful herein are spot gluing; thermal, ultrasonic, or radiative methods of fuse-bonding; stitching, sewing, and other methods of bonding which require the use of mechanical fastening devices; needle-punching and other means. The bonded areas may be randomly (but necessarily evenly) distributed on the layers, or may form any of the patterns described above in the description of low-density regions.

It is important that no appreciable surface of the bonded layers be free of bonds, to prevent loss of the alignment of the layers. It has been found that this goal may be met if the following conditions are observed. The bonded area should comprise about 2% to about 25% of the surface area of the structure. The span between adjacent bond centers should be at least about ¼ inch (6 mm) and no more than about 2 inches (51 mm). The span of a particular bond should be no less than about 1/64 inch (0.40 mm) and no more than about ¼ inch (6 mm).

As explained in the Background Art section above, absorbent structures have many uses. Accordingly, the present invention is useful in the manufacture of many different types of absorbent articles.

The two-sided preferred embodiment of the invention noted above is useful by itself as a towel or wipe which exhibits improved wicking when compared with wipes which are not aligned in accordance with the present invention.

The present invention has utility in connection with bandages and absorbent dressings. The two-layer structures of the present invention may be used in such devices as a topsheet or as an element of the bandage absorbent material.

Catamenial devices of all kinds, such as tampons, panty shields, sanitary napkins and the like all require efficient and reliable absorption, so the materials of the present invention may be used as topsheets or absorbent elements in connection with such devices.

Diapers and other garments for the incontinent require extremely high absorbency to perform their intended function, but great bulk is undesirable in such garments, especially when they are to be worn unobstrusively under outer garments. Accordingly, the wicking benefits exhibited by the present two-layer materials well suit them for use as diaper topsheets and as elements of diaper absorbent cores.

The improvements of the present invention may also be used in surgical drapes, articles of clothing, and other articles. Finally, the uses of the present structure are not limited to disposable garments, for the technology described herein may equally be applied to durable garments.

METHOD DESCRIPTION

Only a brief summary of a method to make articles with improved wicking will be set forth here, for the method has already been described in connection with the preceding description of absorbent articles.

A two-layer structure is made by performing the following steps:
(A) Providing first and second layers of material, each having multiple discrete regions of low density separated by regions of high density;
(B) Placing said first layer in generally parallel relation with respect to said second layer so that a major face of said first layer is immediately adjacent a major face of said second layer;
(C) Aligning said first layer with respect to said second layer, whereby to minimize the percentage of overlap of low density regions of the respective layers;
(D) Bonding said first and second layers to form a unitary object which retains the alignment imparted in step (C).

As already indicated, the percentage of overlap in step (C) is at most a random degree of overlap, is preferably less than a random degree of overlap, and in a most preferred embodiment is 0%.

In a variation of the method described above the alignment step is performed, after the other steps are complete, by selecting from the bonded, randomly aligned two-layer structure those portions of the two-layer structure which have a low degree of overlap. These portions of two-layer materials are surprisingly higher in wicking rate than a random selection of identical structures which are not selected on the basis of overlap.

EXAMPLES AND ANALYTICAL METHODS

Wicking Rate Test—This test measures the rate at which water supplied to a web from a point source (by capillary attraction of the web) is taken up to produce a spot of fluid on the web which has a standard diameter. The test is completely described in *A Method for Measuring the Rate of Absorption of Water by Creped Tissue Paper* (paper presented at the annual meeting of the Technical Section Canadian Pulp and Paper Association, Montreal, Canada, January 24–7, 1967.)

Thermal Conductivity Test—This test was devised to measure the ability of the two-sided wipe described herein as a preferred embodiment of the invention to double as an insulating pad to protect a person's hands from hot metal objects when the latter objects are handled. To perform the test, a pair of identical 100 gram brass weights were heated to 121° C. in an oven; the paired objects were placed side by side.

Panelists were given a three inch (76 mm) square sample of each test material. In one hand each panelist held two thicknesses of a 100% overlapped two-layer sample of material and in the other hand each panelist held two thicknesses of a 0% overlapped sample of two-layer material. They were then asked to pick up a weight with each hand using the samples to protect their fingers. They reported which weight felt the warmest. The samples were rotated so any bias in sensitivity between the right and left hand was eliminated. Results are reported as a percentage of panelists who felt that the object covered with the particular material was hotter.

Percent Overlap Test—The percent of overlap of the low density regions of a first apertured layer with the low density regions of a second apertured layer was determined by placing the materials in a random or deliberate alignment, bonding or clamping them as necessary to preserve the alignment and form a two-layer material, and backing the two-layer materials with a backing of contrasting color (black formica backing under white materials). This procedure caused substantially overlapping areas of low density to become visible as darker regions. (It is believed that better results may be achieved in some cases if a light source, instead of a contrasting backing, is placed behind the two-layer material. The (contrasting) overlapping regions in each of several small samples of material were counted, multiplied by 100%, and divided by the total number of low density areas in the top layer to determine a percentage of overlap. The several determinations of overlap were averaged for each sample, and the mean and standard deviation were calculated for tests in which multiple samples were tested in order to determine a statistical range of percentage of overlap. The latter statistical method was used to determine percentage of overlap for certain materials when the materials were laminated without aligning the low density areas to minimize overlap.

SONTARA Tests—the above tests were conducted on structures with varying degrees of overlap made from two sheets of SONTARA, Model No. 8612. (This material is made according to the processes taught in U.S. Pat. Nos. 4,024,018, 3,563,241, and 3,498,874, which are hereby incorporated herein by reference.) In this material the low-density areas are fairly clean apertures with a density of nearly zero, while the high density materials have densities of about 0.25 g/cc. The basis weight of the material is about 58 grams per square meter, its caliper is about 0.30 mm, the denser of the fibers is 1.5 and the average fiber lengths is roughly 32 mm. The fibers are made of 100% rayon. The apertures have a cross-machine direction span of 0.8 mm and a machine direction span of 1.2 mm. The span of high density "threads" embraced by adjacent apertures is about 0.8 mm in the cross-machine direction and about 0.6 mm in the machine direction. The aperture pattern is a diagonal array wherein alternate machine-direction rows of apertures are staggered by one-half of the center-to-center distance (in the machine direction) between adjacent apertures. In the tests performed herein the layers were stitched together to maintain their alignment. However, when this method is assembled into two-layer articles the layers maybe point bonded with 3.1 mm spots (of acrylic latex glue) in a hexagonal array wherein adjacent spot centers are from 6 to 40 mm apart in the machine direction and 6 to 32 mm apart in the cross-machine direction. Table and lists the results of the above tests performed on stitched SONTARA (Model No. 8612) two-layer structures:

TABLE 1

| % Overlap | Test Result | |
|---|---|---|
| | Wicking Rate | Thermal Conductivity |
| 0% | 4.55 sec | 12.5% |
| 25% | 5.20 sec | * |
| 50% | 5.38 sec | * |
| 75% | 5.82 sec | * |
| 100% | 6.27 sec | 87.5% |

*No data taken

To determine the average percentage of overlap of randomly aligned two-layer structures, 25 samples were analyzed as described above, and the mean and standard deviation were calculated—the former was 42.6% of overlap, and the latter was a standard deviation of 4.5. The highest degree of overlap found was 52%, while the lowest degree of overlap found was 33%. For this material a broad range of percentage of overlap within the scope of the present invention is no more than 58%; a preferred range of percentage of overlap is 0% to about 54%; a more preferred range of percentage of overlap is about 1% to 47%; and a highly preferred range of percentage of overlap of about 1% to 40%.

The wicking test set forth above was performed for a second apertured material sold by DuPont—SONTARA, Model 8411. The latter material is a mixture of 70% rayon fibers and 30% polyester fibers. A first sample was prepared in which the percentage of alignment was about 0%, and a second sample was preferred in which the percentage of alignment was about 100%. The first sample had a wicking rate of 7.0 seconds, while the second sample had a wicking rate of about 15.4 seconds. Thus, a low percentage of overlap is again correlated with good wicking performance.

What is claimed is:

1. An absorbent article with improved wicking performance comprising adjacent first and second layers maintained together intimately in a generally parallel arrangement to form a unitary structure:
   (A) Said first layer comprising a sheet of fibrous material having opposed major surfaces and having multiple discrete regions of low density which penetrate said first layer, and which are separated by regions of high density;
   (B) Said second layer comprising a sheet of fibrous material having multiple discrete regions of low density which are separated by regions of high density;
   wherein 0% of about 58% of the regions of low density of said first layer overlap a region of low density of said second layer;
   and wherein said multiple discrete regions of low density are structures selected from cavities, apertures, holes, slits, areas of widely spaced fibers, and areas of few fibers, separated by said regions of high density.

2. The absorbent article of claim 1, wherein said first and second layers each comprise a sheet of fibrous material having opposed major faces and having multiple discrete regions of low density which penetrate said sheet, and which are separated by regions of high density.

3. The absorbent article of claim 2, wherein said first and second layers are the outside layers of said absorbent article.

4. The absorbent article of claim 3, further characterized as a two-sided wiping article.

5. The absorbent article of claim 1, wherein the adjacent discrete regions of low density of said first and second layers are separated by intervening regions of high density having a span which is at least one-half as great as the largest span of either of said adjacent discrete regions of low density.

6. The absorbent article of claim 5, wherein said low density areas comprise about 10% to about 60% of the aggregate area of said first and second layers.

7. The absorbent article of claim 6, wherein said low density areas comprise about 15% to about 30% of the aggregate area of said first and second layers.

8. The absorbent article of claim 1, wherein said high density and low density areas are further characterized as follows:
   (A) Said high density areas have a density of about 0.05 to 0.5 grams per cubic centimeter;
   (B) Said low density areas have a density of 0 to about 0.45 grams per cubic centimeter; and
   (C) Said high density areas have a density which is at least about 10% higher than the density of said low density areas.

9. The absorbent article of claim 8, wherein said low density regions have a density of 0 to about 0.2 grams per cubic centimeter.

10. The absorbent article of claim 1, wherein said low density regions are holes.

11. The absorbent article of claim 1, wherein said low density areas have a shortest span of at least about 1/64 inch and a longest span of no more than about ¼ inch.

12. The absorbent article of claim 1, wherein said first and second layers are maintained in intimate relation by point bonds.

13. The absorbent article of claim 12, wherein the greatest span of each of said point bonds is no more than about ¼ inch and wherein the smallest span of each of said point bonds is at least about 1/64 inch.

14. The absorbent article of claim 13, wherein the span between the centers of adjacent point bonds is from about ¼ inch to 2 inches.

15. The absorbent article of claim 14 wherein said point bonds cover about 1% to about 25% of the surface area of said article.

16. The article of claim 1 wherein 0% to about 54% of the regions of low density of said first layer overlap a region of low density of said second layer.

17. The article of claim 16, wherein about 1% to about 47% of the regions of low density of said first layer overlap a region of low density of said second layer.

18. The article of claim 17, wherein about 1% to about 40% of the regions of low density of said first layer overlap a region of low density of said second layer.

19. A method to manufacture a two-layer absorbent structure with improved wicking performance, comprising the steps of:

(A) Providing a first layer comprising a sheet of fibrous material having opposed major faces, and further having multiple discrete regions of low density which penetrate said sheet and which are separated by regions of high density;

(B) Providing a second layer comprising a sheet of fibrous material having multiple discrete regions of low density which are separated by regions of high density;

(C) Placing said first layer in generally parallel relation with respect to said second layer so that the inward major face of said first layer is immediately adjacent said second layer;

(D) Aligning said first layer with respect to said second layer, whereby 0% to 58% of the regions of low density of said first layer overlap a region of low density of said second layer; and (E) Bonding said first and second layers intimately together to form a unitary two-layer structure which reforms the alignment imparted in step (C).

20. The method of claim 19, wherein said step (D) is performed by discarding portions of randomly oriented two-layer materials which have a high percentage of overlap.

* * * * *